United States Patent [19]

Johnson

[11] 4,454,118

[45] Jun. 12, 1984

[54] METHOD OF TREATING PSORIASIS

[76] Inventor: Zelma M. Johnson, 1574 Beupre, Madison Heights, Mich. 48071

[21] Appl. No.: 328,866

[22] Filed: Dec. 9, 1981

Related U.S. Application Data

[63] Continuation-in-part of Ser. No. 849,304, Nov. 7, 1977, abandoned.

[51] Int. Cl.$^3$ ..................... A61K 33/22; A61K 35/12; A61K 35/56
[52] U.S. Cl. ..................................... 424/95; 424/148; 424/167; 424/195; 424/343; 424/358
[58] Field of Search .................. 424/95, 358, 343, 148

[56] References Cited

U.S. PATENT DOCUMENTS 3,818,105  6/1974  Coopersmith et al. ............. 424/358
3,824,218  7/1974  McKenna .............................. 424/78

OTHER PUBLICATIONS

Handbook of Non-Prescription Drugs, 5th Ed., 1977, pp. 325–328 & 337–338.
Balsam et al.,–Cosmetics, Science & Technology, 2nd Ed., vol. 1, pp. 5–8, 179–200, 208, 209; vol. 3, p. 393, (1972).
Harry–Modern Cosmeticology, 4th Ed., pp. 111–112, (1955).

*Primary Examiner*—Leonard Schenkman
*Attorney, Agent, or Firm*—Basile, Weintraub & Hanlon

[57] ABSTRACT

A cosmetic composition and a process for alleviating dry skin conditions of the hands, feet, cuticle, neck and facial areas and psoriasis comprising an admixture of lanolin, petrolatum and glycerine. Minor amounts of essential oils and other conditioners can be incorporated.

7 Claims, No Drawings

METHOD OF TREATING PSORIASIS

CROSS REFERENCE TO RELATED APPLICATIONS

This application is a continuation-in-part application of copending U.S. patent application Ser. No. 849,304, filed Nov. 7, 1977 now abandoned for "Cosmetic Lotion", the disclosure of which is hereby incorporated by reference.

BACKGROUND OF THE INVENTION

1. Field of the Invention

This invention relates to cosmetic compositions and a process for alleviating dry skin conditions of the hands, feet, neck, cuticles and facial areas of the human body. More particularly, the invention relates to cosmetic compositions comprising an admixture of lanolin, petrolatum and glycerine.

2. Description of the Prior Art

The cosmetic industry is continually expanding its research efforts in order to provide cosmetic compositions which will moisten and soften the skin, eliminate redness and restore the skin to its natural coloration. The combinations of natural and synthetic substituents employed continue to increase yearly. (see "The Chemistry and Manufacture of Cosmetics" by Maison H. Dehavvare, Second Edition.)

Yet, it will be appreciated that the expansion and growth of the prior art has devolved highly complex synthetic adjuvants for use in the formulations. Thus, organic surfactants, alcohols and the like are incorporated into the compositions of the prior art.

The present invention, on the other hand, employs naturally occurring substances to achieve its purposes.

STATEMENT OF RELEVANT PRIOR ART

To the best of applicant's knowledge the following is the most relevant prior art:
U.S. Pat. No. 1,728,205
U.S. Pat. No. 1,991,501
U.S. Pat. No. 1,920,926
U.S. Pat. No. 2,105,197
U.S. Pat. No. 3,818,105

Additionally, reference can be made to *Modern Cosmetics*, 3rd Ed., pp. 523–524 (1947).

The present invention is distinct from the prior art by its combination of ingredients.

SUMMARY OF THE INVENTION

In accordance with the present invention it has been found that an admixture of lanolin, petrolatum and glycerine is an effective cosmetic lotion for dry skin.

Other ingredients can, also, be incorporated into the basic composition. Thus, minor amounts of cocoa butter, boric acid, and honey can be utilized in admixture with the basic ingredients. These additional adjuvants provide enhanced lubricity to the formulation.

Furthermore, essential oils, such as rose oil, oil of wintergreen, oil of lemon, and the like can be utilized herein to provide an aromatic fragrance to the cosmetic lotion hereof.

The present invention provides, as noted, an improved cosmetic lotion for overcoming the irritation due to chapping, bleeding cracking, as well as dry skin and the like, such as is occasioned from exposure to climatic conditions, including cold weather, excess sun, wind, etc.

For a more complete understanding of the present invention reference is made to the following detailed description and accompanying examples.

DESCRIPTION OF THE PREFERRED EMBODIMENT

In accordance with the present invention there is provided a cosmetic composition comprising, in admixture, (a) lanolin, (b) petrolatum and (c) glycerine.

The cosmetic composition hereof is particularly efficacious, for alleviating the irritation due to chapping, bleeding, cracking and dry skin conditions of the hands, feet, neck, cuticles and facial areas of the human body. In some situations, the composition hereof will alleviate psoriatic conditions.

As noted, the cosmetic composition hereof comprises an admixture of lanolin, petrolatum and glycerine. This mixture is applied to the dry dermal areas of the human body to alleviate "dry skin" condition.

In preparing the present composition, the ingredients are employed in a volumetric ratio of about 1:1:1.2 of lanolin, to petrolatum to glycerine. The ratio of lanolin to petrolatum to glycerine is, preferably, in a volumetric ratio, 1:1:1.5, respectively.

The lanolin product employed herein is deployed as a cream thereof. Thus, either hydrous lanolin, which is available as a topical lubricant or any other commercially available lanolin cream can be used herein.

The petrolatum contemplated for use herein is white petroleum jelly, such as that which is commercially available.

The composition hereof is prepared by mixing together at room temperature and pressure the lanolin and the glycerine. After these two ingredients are thoroughly mixed together, the petrolatum is added thereto. This admixture is then mixed to provide a homogenous mixture of a "cream" consistency.

In order to enhance the lubricity of the present composition, as well as the aromatic fragrance thereof, other adjuvants may be utilized.

Thus, the cosmetic composition may also contain, in addition, other ingredients. Additional ingredients can include boric acid, water, skin lubricants as well as essential oils.

The broic acid is utilized to compensate for "oily" skin. The boric acid employed is, preferably, powdered.

The volumetric ratio of boric acid to lanolin employed herein is about 1:8 to 1:16, respectively. The water is employed to "dilute" the composition to ensure its flowability as a cream, rubber than as a gel. The water is deployed as either distilled or deionized. The water is present in a volumetric ratio to lanolin of about 1:4, respectively.

Any skin lubricant can be employed herein. Representative of such lubricant is cocoa butter. In utilizing the cocoa butter, a cream thereof is employed. The lubricant, which is preferably cocoa butter, is present in a volumetric ratio to lanolin of about 1:4 cocoa butter to lanolin, respectively.

In order to further enhance the lubricity as well as the fragrance of the composition, essential oils may be incorporated thereinto. Suitable essential oils include Oil of Rose, Rose Geranium Oil, Methyl Rhodinone, Bay Rum, Sandalwood, Jasmin, Attar of Rose, Oil of Orange, Oil of Lemon, as well as combinations thereof.

The oils, where employed, are present in a volumetric ratio to lanolin of about 1:16 oil to lanolin, respectively.

Where these additional ingredients are employed the instant composition is prepared by blending the desired quantity of lanolin together with the skin lubricant, the boric acid, water and essential oils, with the glycerine. Thereafter, the petrolatum is added thereto and the admixture is thoroughly mixed. It should be noted that the adjuvants need not all be utilized at one time, but any one, alone, or combination thereof can be used.

For a more complete understanding of the present invention reference is made to the following examples. The following examples are illustrative of the present invention and are not intended in any way as a limitation upon the scope thereof. In the examples, all parts are by volume absent indications to the contrary.

EXAMPLE I

A cosmetic composition was prepared by blending forty parts of white petroleum jelly, forty parts of lanolin, ten parts of cocoa butter and sixty parts of glycerine in the manner described above.

The resulting composition was then applied four times daily to the arms and legs of a woman suffering from psoriasis. Her skin was heavy with scale, with severe bleeding from cracks on her skin. Within four days after applying the composition, the cracks were almost healed and most of the scales had disappeared. Within seven days, the cracks were completely healed, the scale had disappeared and the skin displayed no signs of psoriasis.

EXAMPLE II

A cosmetic composition was prepared by mixing thirty-two parts of lanolin, eight parts of cocoa butter, two parts of boric acid, eight parts of distilled water, forty-eight parts of glycerine, four parts of honey, one part of Rose Geranium Oil, and thirty-two parts of white petroleum jelly. The mixture was well stirred thoroughly mixing the ingredients, in the manner described hereinabove.

EXAMPLE III

To evidence the efficacy of the present invention, a series of individuals suffering from various degrees of dermatological infirmities compared to composition hereof to commercially available products, some of which contain one or more of the component hereof. The results, based upon the persons' personal observations are set forth hereinafter.

| Person | Commercial Products Compared to Present Invention | Results |
|---|---|---|
| 1 | Vaseline Intensive Care Lotion, Pacquins Hand Cream, Jergens Hand Lotion, Sargon, Mazon | Within one wk of use, Invention healed cracks in hands from Psoriatic condition. |
| 2 | Merle Norman Cosmetics, Jergens Direct Aid Lotion, Vaseline Intensive Care Lotion, Johnson's Baby Lotion, Keri Lotion | Invention gave "safer" feel to skin than the products compared thereto. |
| 3 | Nivea, Corn Huskers Lotion, Jergens for Extra Dry Skin, Jergens Direct Aid Hand Lotion, Ponds Lotion, Vaseline Intensive Care Lotion, Mary Kaye Lotions. | Commercial items irritated dry skin condition, whereas Invention, over a year period alleviated dry skin condition. |
| 4 | Jergens Extra Dry Skin Cream, Vaseline, Ponds Cream | Within 2 days after starting use, Invention cleared up chapped hands, commercial items never cleared up dryness. |
| 5 | Moon Drops by Revlon, Vita-Moist by Avon, Jergens Hand Cream, Vaseline Intensive Care Lotion. | User found Invention superior for alleviating dryness over commercial products, each of which were used for extended periods of time. |
| 6 | Johnson's Baby Cream, White Vaseline, Zinc Oxide Ointment, Vitamin E Oil, Boric Acid Ointment, Corn Huskers Lotion. | User had severe dry skin of hands necessitating application of some ointment every night; Vaseline provided best relief but did not heal the cracks due to dryness over a ten year period of usage; Invention healed cracks within 2 weeks of usage. |
| 7 | Nivea, Ponds Cold Cream, Lady Esther Cream, Mary Kaye Creams | Within 2 weeks after beginning to use Invention, dry skin condition alleviated, whereas commercial products failed to help dry skin condition. |

Each of the persons testing the composition hereof, employed the composition of EXAMPLE I.

From the preceding it will be readily perceived that the present invention defines a completely natural product which, not only, alleviates the irritating conditions denoted heretofore, but, which, also, can be used to prevent such irritations from accurring.

Having, thus, described the invention, what is claimed is:

1. A method of treating psoriatic conditions which comprises topically applying an effective amount of a composition consisting essentially of an admixture of lanolin, petrolatum, glycerine and cocoa butter to the skin of a psoriatic subject, the admixture being in a respective ratio of 1:1:1.5:0.25.

2. The method of claim 1 wherein the admixture contains boric acid.

3. The method of claim 2 wherein the boric acid is present in about a 1:8 to 1:16 volumetric ratio of boric acid to lanolin, respectively.

4. The method of claim 1 wherein the admixture contains water.

5. The method of claim 4 wherein the water is present in about a 1:4 volumetric ratio of water to lanolin, respectively.

6. The method of claim 1 wherein the admixture contains essential oils.

7. The method of claim 6 wherein essential oils are present in about a 1:16 volumetric ratio of essential oils to lanolin, respectively.

* * * * *